United States Patent
Selvitelli et al.

(10) Patent No.: US 6,524,315 B1
(45) Date of Patent: Feb. 25, 2003

(54) ORTHOPAEDIC ROD/PLATE LOCKING MECHANISM

(75) Inventors: David M. Selvitelli, Wellesley, MA (US); Martin A. Reynolds, Mansfield, MA (US); Thomas V. Doherty, Foxboro, MA (US)

(73) Assignee: DePuy Acromed, Inc., Raytham, MA (US)

( * ) Notice: Subject to any disclaimer, the term of this patent is extended or adjusted under 35 U.S.C. 154(b) by 40 days.

(21) Appl. No.: 09/633,057

(22) Filed: Aug. 8, 2000

(51) Int. Cl.[7] ................................................ A61B 17/56

(52) U.S. Cl. .............................. 606/70; 606/61; 606/60; 606/71

(58) Field of Search .............................. 606/70, 71, 72, 606/73, 69, 61, 60; 623/17.11, 17.15, 17.16

(56) References Cited

U.S. PATENT DOCUMENTS

| | | | |
|---|---|---|---|
| 4,299,212 A | 11/1981 | Goudfrooy | 128/92 |
| 4,815,453 A | 3/1989 | Cotrel | 128/69 |
| 4,841,959 A | 6/1989 | Ransford | 128/192 |
| 4,887,595 A | 12/1989 | Heinig et al. | 606/61 |
| 5,024,213 A | 6/1991 | Asher et al. | 128/69 |
| 5,127,912 A | 7/1992 | Ray et al. | 606/61 |
| 5,129,900 A | 7/1992 | Asher et al. | 606/61 |
| 5,176,680 A | 1/1993 | Vignaud et al. | 606/61 |
| 5,190,543 A | 3/1993 | Schlapfer | 606/61 |
| 5,217,461 A | 6/1993 | Asher et al. | 606/61 |
| 5,261,912 A | 11/1993 | Frigg | 606/61 |
| 5,306,275 A | 4/1994 | Bryan | 606/61 |
| 5,312,404 A | 5/1994 | Asher et al. | 606/61 |
| 5,360,429 A | 11/1994 | Jeanson et al. | 606/61 |
| 5,443,467 A | 8/1995 | Biedermann et al. | 606/65 |

(List continued on next page.)

OTHER PUBLICATIONS

Uppsala, S.E., "The Cross–Cervical Rod Spinal System: A Multi–Option Posterior Fixation Device for the Cervical Spine," NordOpedic AB (Sep. 1, 1996).

Primary Examiner—Pedro Philogene
(74) Attorney, Agent, or Firm—Nutter, McClennen & Fish, LLP

(57) ABSTRACT

An orthopaedic junction or anchor assembly for anchoring a linkage such as a rod or cable used for fixation or reduction. The assembly includes a slotted bolt that fits through an apertured plate, and a support platform that fits over the bolt, capturing the plate in a one-piece assembly for convenient installation. The base of the bolt is recessed in the plate and a cap or nut tightens down to secure the linking member, e.g., a rod or cable, in the bolt slot, simultaneously clamping the bolt to fix both its position and its orientation on the plate. The support platform has the form of a generally annular washer with an upper surface including a transverse groove on which the rod seats, and a lower surface abutting the plate. A sleeve potion may extend within and buttress the surrounding wall of the plate. The plate may take various forms, such as a hook or offset arm, an occipital T-plate, or a vertebra plate. In one embodiment the support platform is swaged to the bolt, allowing the bolt to rotate freely, and slide along the slot of the bone plate as a captive assembly, keeping all the components together without constraining the alignment during installation. Other embodiments employ mating ridge and groove, or other detents circumferentially on the bolt shaft and the inner face of the support, to snap and retain the pieces together. When the rod or other linkage has been positioned, a lock nut or cap then fastens onto the bolt to seat the rod against the support platform and lock both the position of the bolt and the angular orientation of its slot. Tightening the nut or cap pushes the rod downward to seat on the support plate and pulls the bolt upward to press the base of the bolt against the bottom of the plate. The bottom surfaces of the support washer as well as the plate-facing surface of the base may be roughened or textured to engage the plate, or otherwise increase resistance to rotational and lateral movement once the rod has been positioned and the nut is torqued down.

16 Claims, 7 Drawing Sheets

U.S. PATENT DOCUMENTS

| | | | |
|---|---|---|---|
| 5,490,822 A | 2/1996 | Biedermann | 602/16 |
| 5,498,264 A | 3/1996 | Schlapfer et al. | 606/72 |
| 5,501,684 A | 3/1996 | Schlapfer et al. | 606/73 |
| 5,507,745 A | 4/1996 | Logroscino et al. | 606/61 |
| 5,520,689 A | 5/1996 | Schlapfer et al. | 606/61 |
| 5,534,001 A | 7/1996 | Schlapfer et al. | 606/61 |
| 5,542,946 A | 8/1996 | Logroscino et al. | 606/61 |
| 5,545,164 A | 8/1996 | Howland | 606/61 |
| 5,545,165 A | 8/1996 | Biedermann et al. | 606/61 |
| 5,591,167 A | 1/1997 | Laurain et al. | 606/61 |
| 5,593,408 A | 1/1997 | Gayet et al. | 606/61 |
| 5,601,552 A | 2/1997 | Cotrel | 606/61 |
| 5,601,553 A | 2/1997 | Trebing et al. | 606/61 |
| 5,615,965 A | 4/1997 | Saurat et al. | 403/24 |
| 5,651,789 A | 7/1997 | Cotrel | 606/61 |
| 5,672,176 A | 9/1997 | Biedermann et al. | 606/61 |
| 5,676,640 A | 10/1997 | Biedermann | 602/26 |
| 5,702,395 A | 12/1997 | Hopf | 606/61 |
| 5,702,452 A | 12/1997 | Argenson et al. | 623/17 |
| 5,702,453 A | 12/1997 | Rabbe et al. | 623/17 |
| 5,713,898 A * | 2/1998 | Stucker et al. | |
| 5,716,355 A | 2/1998 | Jackson et al. | 606/61 |
| 5,716,356 A | 2/1998 | Biedermann et al. | 606/61 |
| 5,725,527 A | 3/1998 | Biederdmann et al. | 606/61 |
| 5,741,255 A | 4/1998 | Krag et al. | 606/61 |
| 5,741,258 A | 4/1998 | Klaue et al. | 606/70 |
| 5,743,907 A | 4/1998 | Asher et al. | 606/61 |
| 5,743,911 A | 4/1998 | Cotrel | 606/61 |
| 5,810,823 A | 9/1998 | Klaue et al. | 606/69 |
| 5,814,046 A | 9/1998 | Hopf | 606/61 |
| 5,873,878 A | 2/1999 | Harms et al. | 606/61 |
| 5,879,352 A | 3/1999 | Filoso et al. | 606/62 |
| 5,899,906 A | 5/1999 | Schenk | 606/73 |
| 5,928,233 A | 7/1999 | Apfelbaum et al. | |
| 5,961,517 A | 10/1999 | Biedermann et al. | 606/61 |
| 5,976,135 A | 11/1999 | Sherman et al. | 606/61 |
| 5,976,141 A | 11/1999 | Haag et al. | 606/72 |
| 5,993,449 A | 11/1999 | Schlapfer et al. | 606/60 |
| 6,027,533 A | 2/2000 | Olerud | 623/17 |
| 6,063,090 A | 5/2000 | Schlapfer | 606/61 |
| 6,086,590 A | 7/2000 | Margulies et al. | |
| 6,099,528 A | 8/2000 | Saurat | 606/61 |
| 6,102,912 A | 8/2000 | Cazin et al. | 606/61 |
| 6,106,526 A | 8/2000 | Harms et al. | 606/61 |
| 6,139,548 A | 10/2000 | Errico | 606/61 |
| 6,146,382 A | 11/2000 | Hurlbert | 606/61 |
| 6,168,597 B1 | 1/2001 | Biedermann et al. | 606/73 |
| 6,179,841 B1 | 1/2001 | Jackson | 606/73 |
| 6,187,005 B1 | 2/2001 | Brace et al. | 606/61 |
| 6,187,009 B1 | 2/2001 | Herzog et al. | 606/75 |
| 6,273,889 B1 * | 8/2001 | Richelsoph | |
| RE37,479 E * | 12/2001 | Kuslich | |

* cited by examiner

ORTHOPAEDIC ROD/PLATE LOCKING MECHANISM

BACKGROUND

The present invention relates to fixation devices used in orthopaedic surgery and particularly to devices used for the reduction of fractures or the positioning of bones by means of a plate attached to a bone or bone fragment in one region and secured to a rod which attaches to a cable, wire, plate or screw fastened in another region. The rod thus attaches between two bone regions for effecting stabilization, positioning, reduction or fixation of the bones.

A number of such mechanisms are known, among which should be mentioned the Harms T-plate which employs a split or slotted bolt, the head of which slides in a slot of a plate that is attached to a bone or bone fragment. The plate accepts the slotted bolt from the bottom and has several channels or grooves extending in different directions in the plate to allow positioning and alignment of the bolt along any one of the distinct channels. In use, a connecting rod fits through the slotted bolt and is captured by a nut which, when tightened, locks the bolt in its position in the channel, and secures the rod in the slot. In general, the system employs a slotted bolt with a square flange at its base so that each of the channels defines orientation of the rod-receiving slot of the outwardly protruding portion of the bolt. The plate thus provides a range of linear positions along several discrete lines, each at a fixed angular orientation, for the rod anchor point.

In addition to such plates, for posterior cervical fixation there also exists a number of eye screws that screw directly into the bone at a single fixed position. In these screws, the eye structure generally is an open slot or other rod-receiving open form adapted to receive the rod therein before being closed by a cap. The cap may be a conventional threaded locking nut, or in some constructions may be a dovetailed cap segment which slides in and wedges against the rod to secure the rod while closing the receiving slot at its open end. Such eye screws may also, in some constructions, be employed to secure a plate to the bone in addition to gripping the stabilization rod. When so used, the plate serves to strengthen the attachment and distribute the stresses coupled by the anchoring screw.

One variant of a rod-receiving fixation screw is the Moss-Miami polyaxial screw, as shown in U.S. Pat. No. 5,672,176. In that device, the screw has a spherical head. A slotted rod-holding cap structure having a conically tapering inner surface fits about the outside of the spherical head in the manner of a ball and socket joint. The rod-holding cap structure is internally threaded and is provided with a number of shaped packing or pressure-bearing inserts with an overall structure that tightens about the spherical screw head as the cap is drawn upward forcing the head down the cone angle. The cap may be rotated before tightening on the spherical head, so this clamping connection allows the rod-holding member to be bolted down and fixed with its slot oriented at an arbitrary angle in rotation about the axis of the screw. The rod fits through the slot in the holding cap structure and is secured by tightening a bolt into the threaded cap. The unit comes as a preassembled device with the packing or pressure-bearing members positioned internally about the ball end of the screw and held by swaging part way up the cap. Tightening of the cap against the rod then draws the conical outer holding body upward against the ball, fixing the slot orientation with the rod in position.

When the underlying bone has sufficient integrity, such individual eye screws offer great flexibility in rod orientation in one plane. Also, when a bone plate secured by multiple screws is necessary, the Harms plate offers a range of clamping point translational positions with a discrete set of angular orientations for connecting a cable, fixation rod or reduction rod. However, each of these systems has its own limitations as to convenience, or as to the range of position or orientation, or to the degree of loading that it may accommodate.

Accordingly, it would be desirable to provide a bone plate and rod junction system of adjustable angulation.

It would also be desirable to provide a multi-axis rod connection that is freely positionable along a slotted plate.

It would also be desirable to provide a multi-axis rod connection in which the components are preassembled to be installed as a unit during surgery.

SUMMARY OF THE INVENTION

One or more of the foregoing desirable ends are achieved in accordance with the present invention by a rod junction mechanism including a slotted bolt, a rod support platform that fits over the bolt, and a nut which tightens down to secure a rod in the slot on the support platform. The base of the bolt is configured to ride in a slot or a counter-bored aperture or channel in a plate or offset tab and is round so it rotates freely in the plate, while the support platform has the form of a generally annular and thick washer that lies over the base of the bolt to sandwich the plate therebetween and clamp firmly in position. The washer has an upper surface possessing a rounded groove on which the rod lies and a lower surface with a step collar that extends within and buttresses the walls of the opening in the plate. The plate is sandwiched between the base of the bolt and the support platform, distributing stress over a wide area while providing a strong anvil to support the rod.

In one embodiment the support platform has lateral openings that extend radially to a depth close to, but not through, its radially inner wall surface so as to leave a thinned wall portion. The bolt is placed through the plate and the platform is swaged to the bolt at the thinned wall portion so as to capture the bone plate therebetween, providing a single-piece assembly for convenience of handling and installation. In this configuration, the bolt may move freely within the bone plate opening as a captive assembly, easing placement during surgery by keeping all the components together. The swaging fixes alignment of the groove of the support plate form along the direction of the slot of the bolt, while leaving both pieces free to rotate, and when the plate opening is a slot, to translate along the slot of the bone plate. Rather than swaging, a preferred embodiment implements a one-piece assembly by providing a circumferential groove and a corresponding ridge on the bolt shaft and the support platform, to function as a snap ring and retain the two parts together during handling and use. In use, once the rod is positioned in the upwardly extending bolt slot, a locking nut or cap, which may be of conventional type, threads onto the bolt. The nut forces the rod against the support platform which, in turn, pushes downward against the bone plate while the nut also pulls the bolt upward, forcing the bolt base flange against the bottom of the plate. The bottom surface of the support platform, the plate-facing surface of the bolt flange, and/or the surface(s) of the plate may be roughened or toothed so as to enhance gripping and increase resistance to rotational or lateral movement of the bolt once the rod has been positioned and the nut torqued down.

BRIEF DESCRIPTION OF THE DRAWINGS

These and other features of the invention will be understood from the description herein, taken together with drawings of illustrative embodiments, wherein

FIGS. 9–9B illustrate another embodiment of a support washer assembly of the present invention;

DETAILED DESCRIPTION

Figure 1:
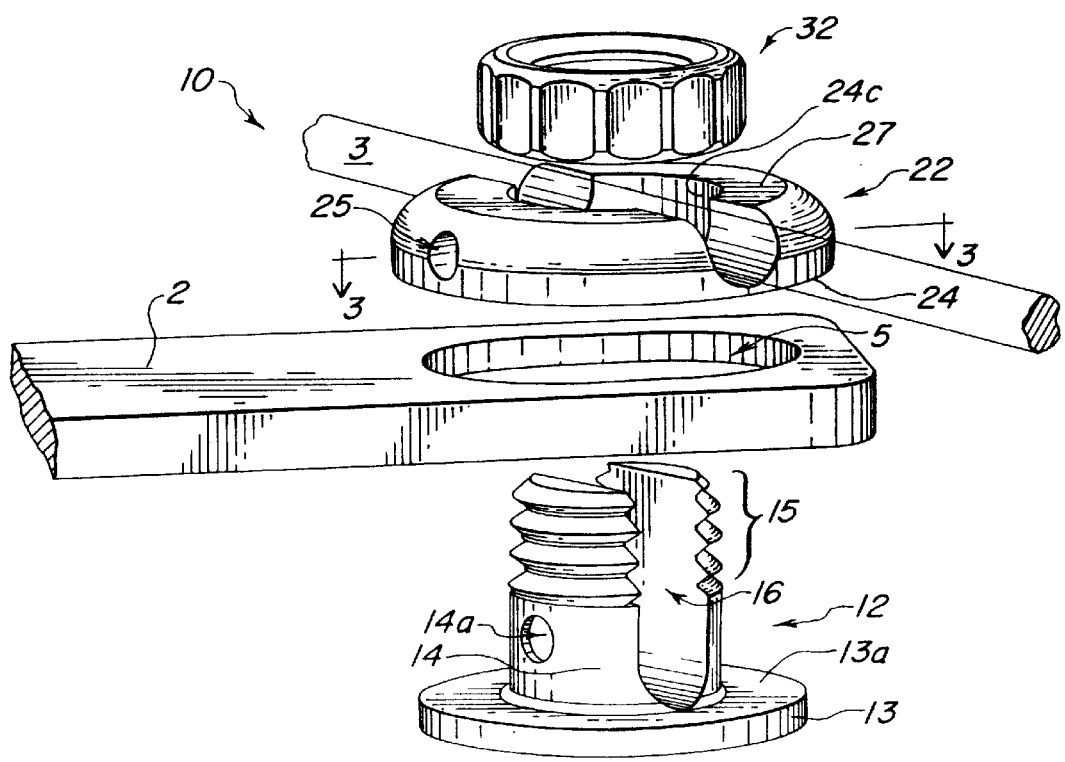
FIG. 1 shows an exploded perspective view of the rod junction system of the present invention.

FIG. 1 shows an exploded perspective view of one embodiment of the rod junction system 10 of the present invention. As shown, in this embodiment, the invention is comprised of a plate 2 through which a slotted bolt 12 fits, with a rod-contacting support platform 22 or support collar fitted over the bolt 12, and a nut or cap 32 fitted onto the end of the bolt to secure the rod. Rod 3 is shown in phantom for purposes of illustration. The aperture 5 in the plate 2 may be a simple round hole, an elongated but closed-ended slot as illustrated, or an open-ended slot of the type known in the prior art that allows the bolt 12 to be moved to various positions along the plate length. Furthermore, the plate may take any of a number of configurations of the various shapes commonly used in orthopaedic fixation. That is, the plate may be generally planar, and shaped like a strip, an L- or a T-shape, or it may be a short tab, adapted to extend laterally from a bone fixation point to position the bolt 12 at an offset or out-of-plane position for clamping the rod 3. It may also be curved out-of-plane to fit a curved bone surface. In a preferred embodiment, the assembly is used with a plate 2 that has the contour of an occipital bone fixation plate.

The hole or slot 5 is counter-bored or milled to a larger opening 5a, so that the base 13 of the slotted bolt fits up in and is recessed from the level of the bottom surface of the plate 2, against a step or thrust face 5b. Thus, the opening 5 may be a counter-bored hole or elongated hole, or one of several step-walled slots. As further shown in FIG. 1, the bolt 12 includes a shank portion 14 extending from the base 13, and a threaded shaft portion 15 extending above the shank. A U-shaped slot 16 runs the length of the threaded shaft 15 and preferably extends through at least a portion of the shank 14. Furthermore the base 13 in the illustrated embodiment is generally disk-shaped or radially symmetric in that it allows the bolt 12 to rotate freely in the hole or slot of plate 2 through one full revolution. The base 13 is considerably wider than the hole 5, so the bolt 12 cannot be pulled through the plate.

On the other side of the plate 2, the support platform 22 or thrust collar fits around the threaded shaft of the bolt and has a shallow yoke or transverse groove 26 (FIG. 3) formed in its top surface 27. In use, groove 26 aligns with the slot 16 of the bolt 12, and forms a bearing or seating surface on which the rod 3 rests. The support platform 22 is formed as an annular washer that functions as a support anvil for the rod 3 and also as a collar or sleeve about the bolt 12. It thus operates together with the bolt to reinforce the apertured plate 2 and effectively sandwich the plate between the base 13 of the bolt and the platform 22 itself.

Figure 3:
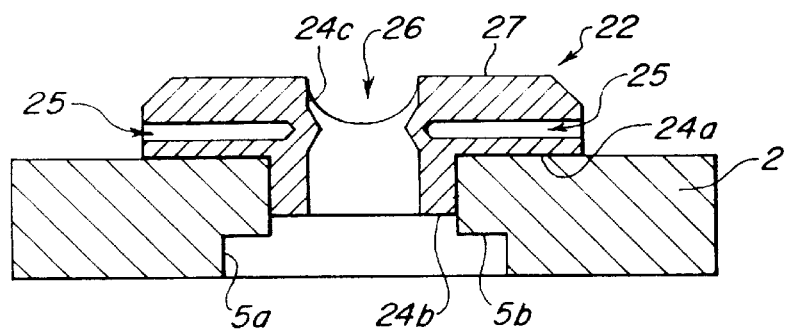
FIG. 3 shows a cross-sectional view through the system of FIG. 1.

As further shown in the vertical sectional view of FIG. 3 taken in a diametral plane of the bolt transverse to the direction of the slot, for this purpose the platform 22 has a lower surface 24 comprised of a washer-like body portion with an outer peripheral surface in a band 24a that rests on the top of the plate 2, and an inner annular portion 24b which extends into the plate opening 5 and forms a collar or reinforcement sleeve within the opening 5 of the plate 2. In this embodiment, a pair of radially directed holes 25, of which one is visible in FIG. 1, extend inward from the circumferentially outer wall of the platform 22 to a depth close to its radially inner surface 24c. As best seen in FIG. 3, the holes 25 serve as access holes to permit swaging the remaining thin-walled inner collar portion of the support platform member 22 to the bolt 12 while the plate 2 is captured between the bolt base 13 and the platform 22, so that the entire assembly forms a single unit loosely held together and freely movable without danger of losing the parts during handling prior to installation.

In the embodiment illustrated in FIGS. 1 and 2, the components are dimensioned so that the platform 22 is swaged to the shank 14 of the bolt below the threaded region 15, and at positions transverse to the axis of the slot 26. For this purpose cross-holes or recesses 14a are preferably drilled or otherwise formed in the shank at positions corresponding to the deformed swaging of the inner wall. Like the base 13 of the bolt 12, the platform 22 extends radially outward beyond the aperture 5 so that when it is swaged together with the bolt, the plate 2 is captured therebetween while the bolt and support platform assembly 12, 22 may rotate freely together as a unit to any angular position in a plane transverse to the axis of the bolt shaft. As shown, the unthreaded shank portion 14 of the bolt extends for a length roughly equal to the thickness of plate 2 and platform 22, and the threaded portion of the shaft 15 extends for a sufficient further length to allow the nut 32 to clamp the rod and bolt assembly together.

Figure 2:
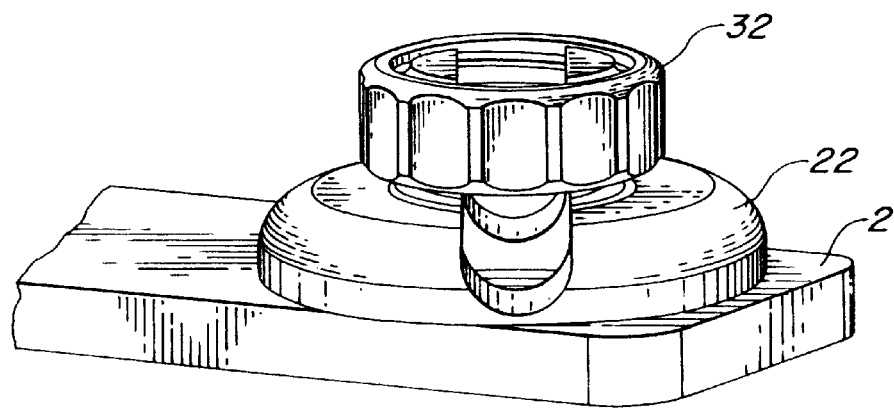
FIG. 2 shows elements of the embodiment of FIG. 1 seated on a plate.

FIG. 2 shows the platform 22 resting in position on the plate 2, with the bolt 12 omitted for clarity. As shown, the thickness of the support platform 22 constitutes a substantial structural reinforcement of the plate anchoring area. The groove in the platform member may taper inward slightly toward its base so that when the rod 3 is inserted in the slot and clamped downwardly, it wedges or fits closely against the sides of the supporting groove, adding rigidity to the overall system. The overall length of the bolt 12 is preferably such that the threaded portion extends only slightly, for example, less than a centimeter, above the top of the platform 22 to accommodate the nut 32, and the nut thus resides with a low profile over the rod and plate once it has been installed.

Figure 11:
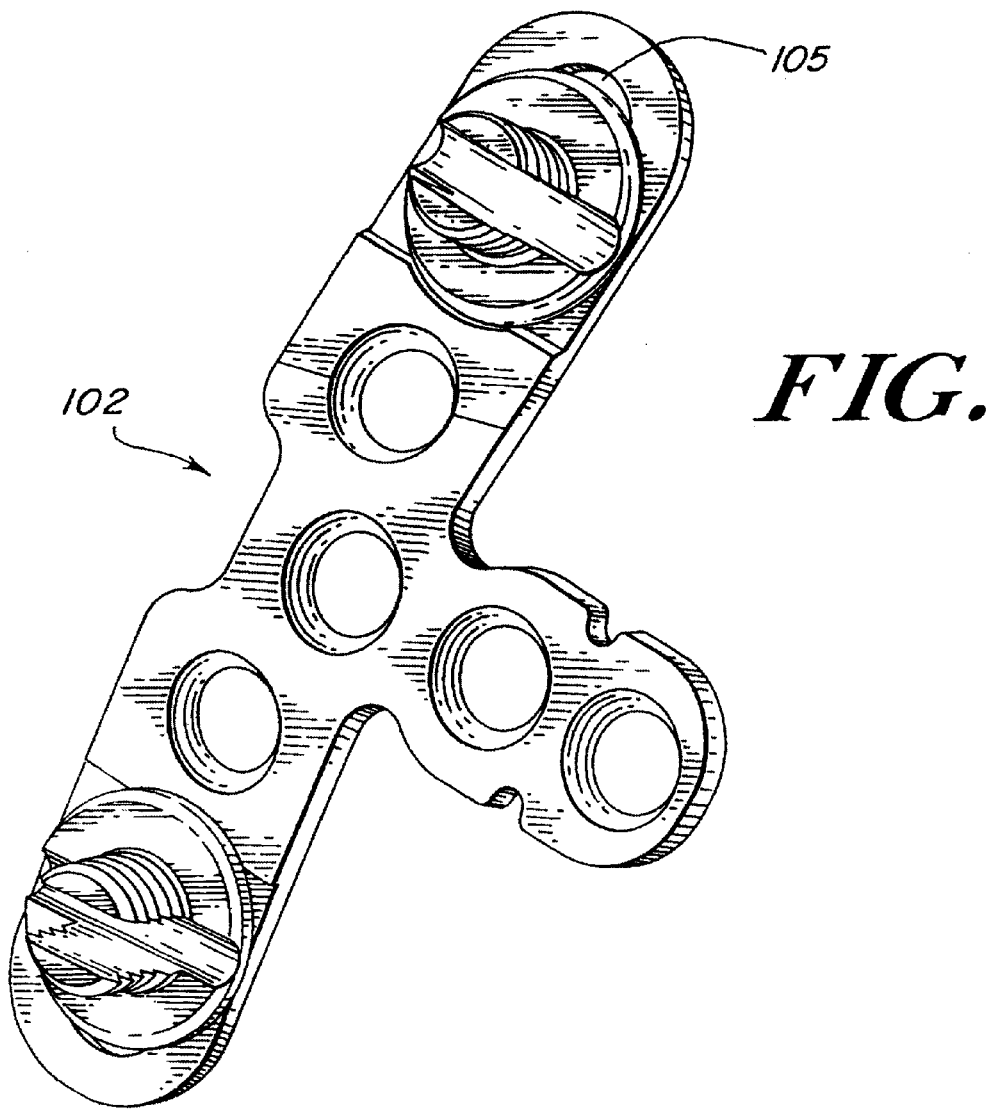
FIG. 11 shows a preferred occipital fixation plate for use in an assembly of the present invention.

FIG. 11 shows by way of example a preferred occipital fixation plate 102 for use with the present invention. Plate 102 includes two apertures 105, each of which accommodates a slotted bolt assembly which may be any of the embodiments shown in the figures herein or their equivalents. As shown, for the occipital plate 102 the apertures 105 are elongated in the lateral direction to allow adjustment of bolt position in a side-to-side direction before tightening down to secure a rod, cable or other fixation linkage.

Figure 5:
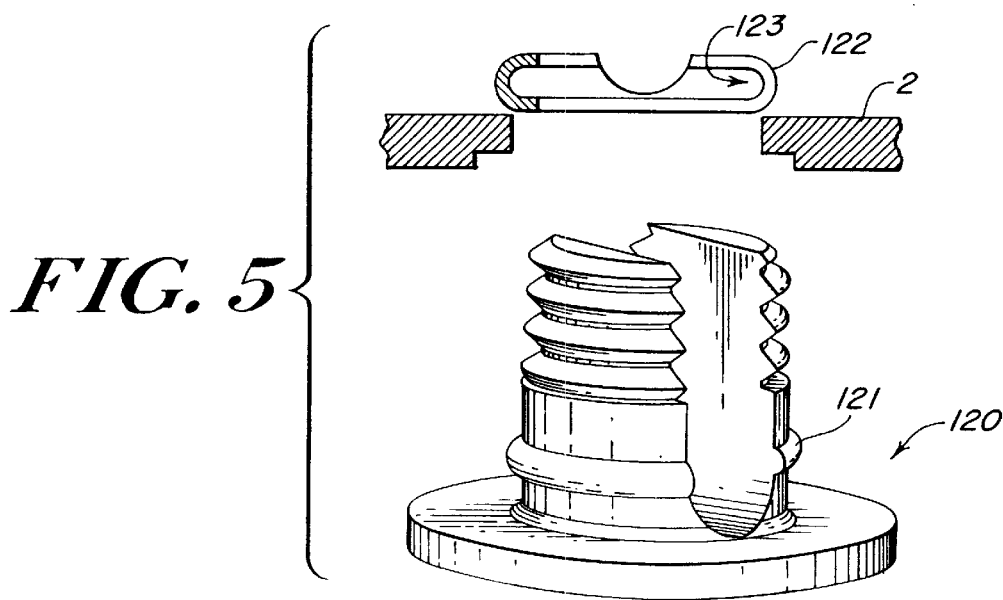
FIG. 5 illustrates another embodiment of an anchor bolt and support washer in accordance with the invention.
Figure 5A:
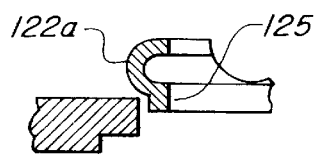
FIG. 5A illustrates another embodiment of a support washer.

In addition to the above described bolt and swaged support washer assembly that capture the plate to form a conveniently installed one-piece plate and anchor assembly of versatile angulation to secure a fixation rod, the invention contemplates other embodiments. FIG. 5 illustrates one such embodiment, wherein an anchor bolt 120 is formed with a protruding circumferential ridge 121 positioned to capture the support washer 122 in a unitary assembly. The support washer 122 in this case has a corresponding groove or recess 123 into which the ridge fits to lock the washer onto the bolt and capture the plate 2. This grooved support washer may have a somewhat lower profile than that illustrated in FIGS. 1–3. Further, it need not have a structural portion corresponding to the dependent sleeve portion 24b of the first-described embodiment, although such a portion may be provided as a centering collar or sleeve 125 shown in FIG. 5A for the support washer 122a.

Figure 6:
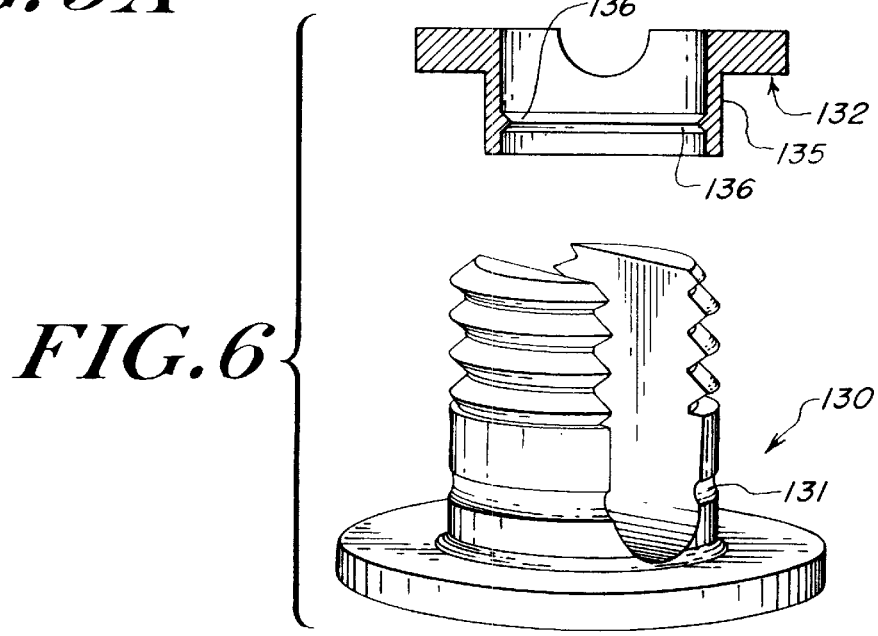
FIG. 6 shows another embodiment of an anchor bolt and support washer in accordance with the present invention.

FIG. 6 shows another embodiment of an anchor bolt and support washer, 130, 132 in accordance with the present invention. As with the other embodiments, the two pieces fasten together to capture the bone plate and provide a nonseparating and unitary assembly that may be freely manipulated during installation, and that allows the slotted bolt to be adjusted in angle, and in some embodiments also in linear position, prior to tightening down of the bolt over the rod or cable linkage assembly. In the embodiment of FIG. 6, the bolt 130 possesses a recessed circumferential groove 131, and the support washer 132 has a corresponding portion with a protruding ridge 136 that snaps into the groove 131 to retain the two parts together. Ridge 136 need not be a continuous ridge, but may consist of one or a small number of slight bumps or protrusions which are sized to allow movement into the groove 131 with a slight pressure, and without shearing or cracking of the contacting parts. When bumps rather than a ridge are provided, the groove 131 may also be replaced by a few discrete indentations, in which case the indentations and bumps may further be positioned at angles selected to align the bolt slot with the rod support groove. A dependent collar portion 135 allows the mating ridge 136 or protruding bumps to be positioned quite low on the bolt shank, so that the device has an overall profile that extends only slightly above the plate to which it is mounted.

Figure 7:
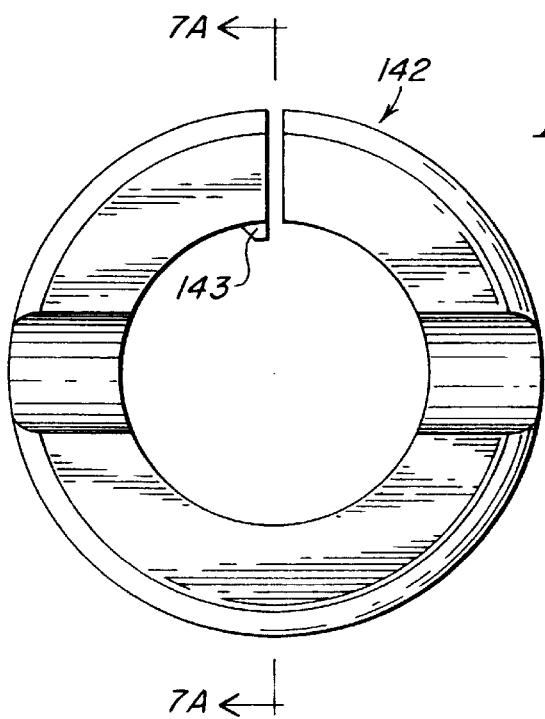
FIGS. 7–7B illustrate another embodiment of a support washer for the practice of the present invention.
Figure 7A:
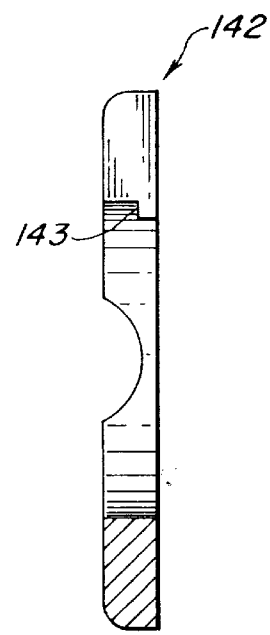
Figure 7B:
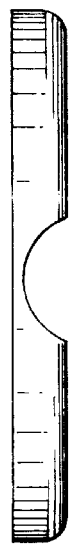
Figure 8:
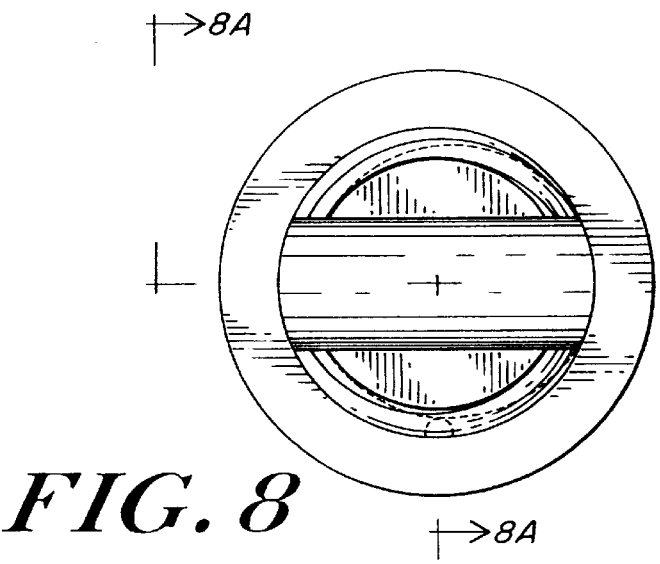
FIGS. 8–8A illustrate an anchor bolt of the present invention for use with the support washer embodiment of FIGS. 7–7B.
Figure 8A:
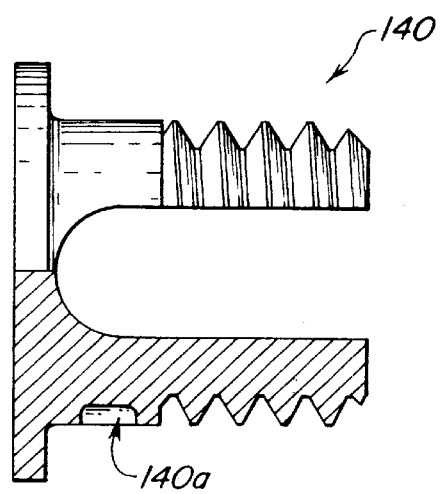
Figure 9:
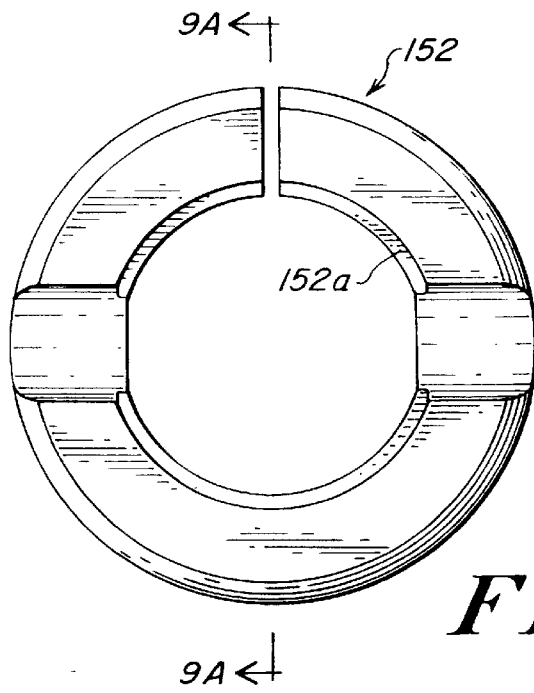
Figure 10:
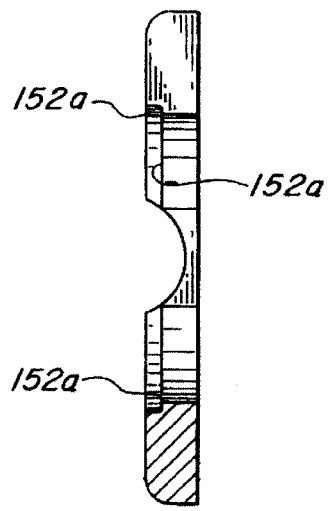
FIGS. 10 and 10A illustrate an anchor bolt embodiment for use with the washer assembly of FIGS. 9–9B.
Figure 10:
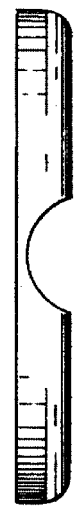
Figure 10:
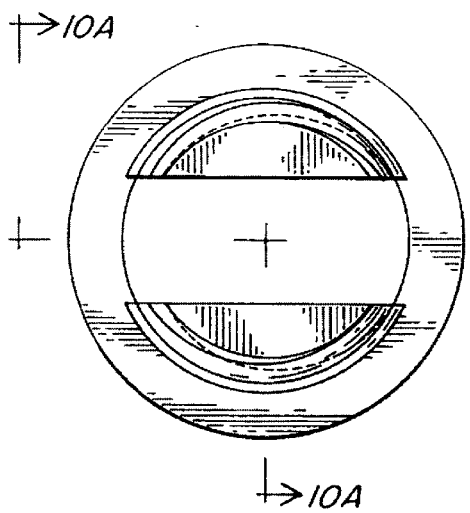
Figure 10A:
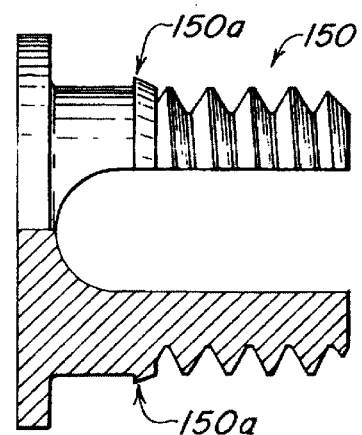

FIGS. 7–7B and 8–8A illustrate another embodiment of an orthopaedic anchor bolt 140 and support washer 142 for the practice of the present invention. As with the other embodiments, the washer has a transverse groove or seating surface for supporting the fixation rod or cable, and has a generally flat washer-like body that rests against the underlying bone plate. In the embodiment of FIG. 7 the washer 142 is preferably a split washer having a radially extending gap 142a that allows the washer to flex open and be placed over the bolt 140 such that a tooth 143, which projects radially inward, engages a corresponding recess 140a in that bolt. FIG. 7 shows the washer in a top plan view, while FIG. 7A illustrates a vertical section taken along a diametral plane and through the washer gap 142a. FIG. 7B shows a side plan view, illustrating the flat upper and lower surfaces of the washer. FIG. 8 is an end view of the bolt, 140, taken along the axial direction from above the slot of the bolt, with a dotted section line illustrated by A—A showing the direction of the partial cut away sectional view of FIG. 8A. As shown in FIG. 8A a recess 140a approximately one millimeter deep is provided in the bolt shank to capture the protruding tooth 143 of the support washer.

FIGS. 9–9B, 10 and 10A illustrate another embodiment of an anchor bolt and washer assembly 150, 152 of the present invention. These views correspond to those of FIGS. 7–7B, 8 and 8A, with similar features appearing similarly in the two figures. In this embodiment, however, bolt 150 is provided with a catch or radially-protruding and sharply angled edge 150a extending radially outward near the top of the shank portion of the bolt. The catch 150a catches the radially inward edge 152a of an upper surface of the support washer 152. For this purpose the radially inner region of the support surface is recessed slightly in the axial direction, so that the fastening edge 152a of the support washer 152 is lowered, at the level of the shank of the bolt 150. The entire assembly therefore has a low profile. The recessed inner step also protects the fastening edge from becoming nicked, rounded or otherwise impaired if a bulk finishing process such as tumbling, is employed to deburr or finish the support washer.

Thus, the anchor assembly may be implemented with a number of different possible washer or collar-like support elements to capture the plate and provide a freely-oriented anchor bolt assembly. The plate itself may take varied forms, including individual vertebra plates, hooks or offset elements, or may be shaped like an occipital T-plate, forming an assembly with one or more anchor bolts.

This completes a description of a number of representative embodiments of an orthopedic fixation device in accordance with the present invention.

While not specifically illustrated, the aperture 5 in the plate may be a circular hole, or an elongated hole or may be an open-ended or a closed-ended slot. In the latter three cases, the bolt 12, in addition to being fully rotatable about its axis, may slide to an arbitrary linear position along the slot before it is tightened in position. The upper surface 13a of the base of the bolt (FIG. 1), as well as the lower surface 24a of the support platform (FIG. 3), may be toothed, knurled, roughened or otherwise textured to assure that these surfaces grip the plate when tightened and prevent the bolt from rotating or shifting position. Alternatively, the corresponding contact region of the plate may have such a gripping texture or surface finish. Furthermore, the plate component may have plural openings, grooves or channels adapted to receive one or more bolt/collar assemblies of the invention, and may have several grooves extending along different directions to provide a range of position options. The bolt and support plate may also be secured to each other by detents or interference fit of other configuration than those illustrated in the figures.

Figure 4:
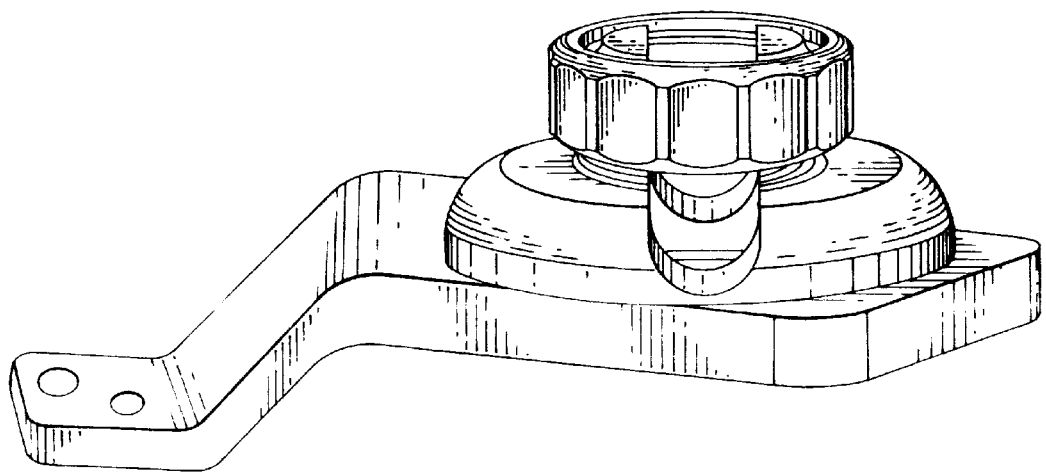
FIG. 4 illustrates an offset tab embodiment.

The invention has particular utility as an occipital fixation assembly, wherein the plate portion is shaped to firmly seat against the occiput. However, the ability to conveniently provide a complete rotation of the rod-receiving slot while allowing some translation or offset is of utility in diverse other embodiments, wherein the plate portion of the assembly is configured in various lengths or shapes, such as an offset tab embodiment as shown in FIG. 4, short vetebra plates, and other shapes adapted to specific applications.

The invention being thus disclosed and illustrative embodiments depicted herein, further variations and modifications of the invention, will occur to those skilled in the art, and all such variations and modifications are considered to be within the scope of the invention, as defined by the claims appended hereto and equivalents thereof.

What is claimed is:

1. An orthopaedic fixation assembly, comprising:
   a bone plate having a front face, a back face and an elongate aperture extending through the front and back faces, the bone plate being securable to a bone;
   a bolt having a bolt base, a bolt shaft and a slot in the shaft, the bolt being sized for insertion through the aperture so that the bolt base contacts the back face of the bone plate, the bold shaft extends through the front face of the bone plate, and the bolt is rotatable within the aperture and movable along the aperture in a direction in which the aperture is elongated; and
   a support platform consisting of a single washer having a back face and an opposed front face, the support platform configured to fit about the bolt shaft so that the back face of the support platform rests against the front face of the bone plate and the front face of the support platform cooperates with the slot for holding an elongate bone fixation element;
   wherein the bolt and the support platform are adapted to be secured together to hold the bone plate between the bolt base and the back face of the single support platform.

2. The assembly of claim 1, wherein the support platform includes a sleeve portion that fits within the aperture.

3. The assembly of claim 2, wherein the support platform sleeve portion extends partially through the bone plate.

4. The assembly of claim 1, wherein the back face of the bone plate has a counter-machined recess around the aperture and the bolt base is round and fits within the counter-machined recess for rotation therein.

5. The assembly of claim 1, wherein the bolt shaft has an outer diameter in a support platform mating region and a radially protruding element that extends outwardly beyond the bolt shaft outer diameter and the support platform is formed as a split washer and expands to slide over the radially protruding element and reverses its expansion to be captured by the radially protruding element.

6. The assembly of claim 5, wherein the radially protruding element is a protruding circumferential ridge.

7. The assembly of claim 5, wherein the bolt shaft outer diameter is defined within a recess on the bolt shaft.

8. The assembly of claim 7, wherein the recess is circumferential.

9. An orthopaedic fixation assembly, comprising:
   a bone plate having a front face, a back face and an elongate aperture extending through the front and back faces, the bone plate being securable to a bone;
   a bolt having a bolt base, a bolt shaft and a slot in the shaft, the bolt having an outer diameter in a support platform mating region and being sized for insertion through the aperture so that the bolt base contacts the back face of the bone plate, the bold shaft extends through the front face of the bone plate, and the bolt is rotatable within the aperture and movable along the aperture in a direction in which the aperture is elongated; and
   a support platform in the form of a split washer having a back face and an opposed front face, the support platform configured to fit about the outer diameter of the bolt shaft so that the back face of the support platform rests against the front face of the bone plate and the front face of the support platform cooperates with the slot for holding an elongate bone fixation element;
   wherein the bolt shaft includes a radially protruding element that extends outwardly beyond the bolt shaft outer diameter and the support platform expands to slide over the radially protruding element and reverses its expansion to be captured by the radially protruding element.

10. The assembly of claim 9, wherein the support platform includes a sleeve portion that fits within the aperture.

11. The assembly of claim 10, wherein the support platform sleeve portion extends partially through the bone plate.

12. The assembly of claim 9, wherein the back face of the bone plate has a counter-machined recess around the aperture and the bolt base is round and fits within the counter-machined recess for rotation therein.

13. The assembly of claim 9, wherein the radially protruding element is a protruding circumferential ridge.

14. The assembly of claim 9, wherein the bolt shaft outer diameter is defined within a recess on the bolt shaft.

15. The assembly of claim 14, wherein the recess is circumferential.

16. The assembly of claim 9, wherein the aperture is elongated and the assembly includes a single support platform.

* * * * *